(12) United States Patent
Harvey et al.

(10) Patent No.: US 11,667,737 B1
(45) Date of Patent: Jun. 6, 2023

(54) THERMOSETTING POLYIMIDES DERIVED FROM RESVERATROL

(71) Applicant: The United States of America, as represented by the Secretary of the Navy, Arlington, VA (US)

(72) Inventors: Benjamin G. Harvey, Ridgecrest, CA (US); Andrew Chafin, Ridgecrest, CA (US); Matthew C. Davis, Ridgecrest, CA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 34 days.

(21) Appl. No.: 17/513,133

(22) Filed: Oct. 28, 2021

Related U.S. Application Data

(62) Division of application No. 16/431,790, filed on Jun. 5, 2019, now Pat. No. 11,192,967, which is a division of application No. 15/415,278, filed on Jan. 25, 2017, now abandoned.

(51) Int. Cl.
| | | |
|---|---|---|
| *C07C 209/22* | (2006.01) | |
| *C07C 211/51* | (2006.01) | |
| *C07C 217/90* | (2006.01) | |
| *C07C 235/20* | (2006.01) | |
| *C08F 132/08* | (2006.01) | |
| *B01J 19/12* | (2006.01) | |
| *C07D 235/20* | (2006.01) | |
| *C08K 7/04* | (2006.01) | |

(52) U.S. Cl.
CPC .......... *C08F 132/08* (2013.01); *B01J 19/123* (2013.01); *C07C 209/22* (2013.01); *C07C 211/51* (2013.01); *C07C 217/90* (2013.01); *C07D 235/20* (2013.01); *C08K 7/04* (2013.01)

(58) Field of Classification Search
CPC .... B01J 19/123; C07C 209/22; C07C 211/51; C07C 217/90; C07C 235/20
USPC .......................................................... 532/1
See application file for complete search history.

(56) References Cited

PUBLICATIONS

Sun et al.(Bioorganic & Medicinal Chemistry. vol. 18, pp. 5352-5366 (2010)) (Year: 2010).*
Kondratyuk et al.(Mol Nutr Food Res . . . vol. 55(8), pp. 1249-1265 (2011)) (Year: 2011).*

* cited by examiner

*Primary Examiner* — Kelechi C Egwim
(74) *Attorney, Agent, or Firm* — Naval Air Warfare Center Weapons Division; Stuart H. Nissim

(57) ABSTRACT

A method for making thermosetting polyimides from resveratrol including converting resveratrol to trisaniline, reacting trisaniline with one or more dianhydride and thermosetting endcap to form amic acid, thermally imidizing amic acid to form polyimide oligomer, and cross-linking polyimide oligomer with heat and pressure to generate polyimide thermoset.

1 Claim, 6 Drawing Sheets

THERMOSETTING POLYIMIDES DERIVED FROM RESVERATROL

CROSS-REFERENCE TO RELATED APPLICATIONS

This is a divisional, non-provisional application claiming the benefit of parent application Ser. No. 16/431,790 filed on Jun. 5, 2019 which was divisional, non-provisional application claiming the benefit of parent application Ser. No. 15/415,278 filed on Jan. 25, 2017, whereby the entire disclosure of which is incorporated herein by reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to thermosetting polyimides that are used in a wide variety of military and commercial platforms. Methylene dianiline is a key component of several formulations but is highly toxic, mutagenic, and a suspected human carcinogen. The current invention describes new polyimides based on trifunctional anilines that have similar or higher glass transition temperatures compared to conventional resins.

Figure 1:
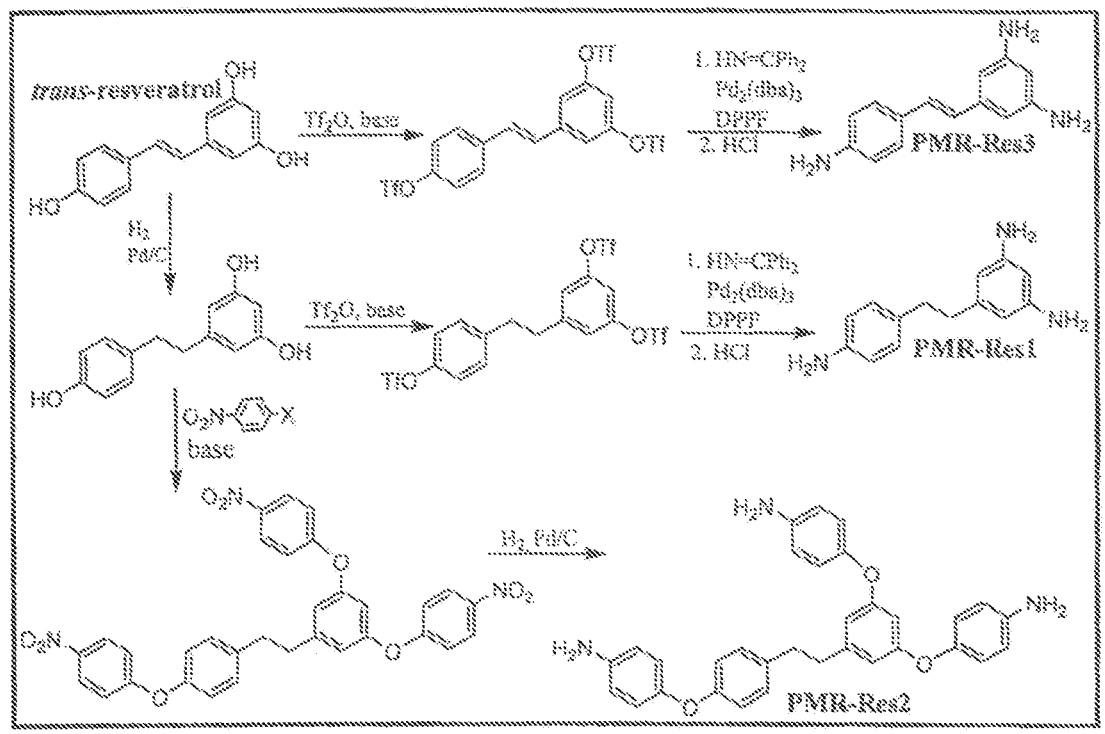
FIG. 1 is a chemical flow chart showing the synthesis of trisanilines, according to embodiments of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF THE EMBODIMENTS OF THE INVENTION

Embodiments of the invention generally relate to thermosetting resins incorporating trisanilines prepared from resveratrol have comparable or even higher glass transition temperatures compared to conventional resins, can be produced from sustainable feedstocks and have significantly lower toxicity than those synthesized from methylene dianiline.

Methylene dianiline (MDA) is used extensively by industry and the DoD in polyurethanes, as a hardener in epoxy resins, and as a component of thermosetting polyimide resins. Although MDA imparts excellent mechanical properties to derivative resins, it is highly toxic with an occupational exposure limit of only 10 ppb averaged over an 8-hour workday. MDA is a potent liver toxin, mutagenic, and a suspected human carcinogen.

This invention describes new trisanilines that can be prepared from a sustainable feedstock and that have significantly lower toxicity than MDA. The use of these trisanilines in polyimide formulations results in thermoset materials with glass transition temperatures comparable to or higher than MDA. In addition these new polyimide formulations have outstanding oxidative stability, and processing characteristics similar to MDA.

U.S. Pat. No. 5,145,943 describes PMR resins prepared from MDA, BTDA, and NA. U.S. Pat. No. 5,171,822 claims "low toxicity" PMR formulations using 3,4-oxydianiline. Also see U.S. Pat. Nos. 9,187,591, 9,127,115, 9,051,414, 9,018,314, 8,993,689, 8,993,688, and 8,921,614.

1. Resveratrol is isolated from a plant source, synthesized from renewable phenols, or prepared from a petroleum source.
2. Resveratrol is converted to a trisaniline or, resveratrol is hydrogenated and converted to a trisaniline.
3. Alternatively resveratrol is allowed to react with a halogenated nitroaromatic compound to form a nitrated species which is then reduced to a trisaniline.
4. A trisaniline is allowed to react with a dianhydride [e.g. 3,3,',4,4'-benzophenonetetracarboxylic dianhydride (BTDA)] and 5-norbornene-2,3-dicarboxylic anhydride (NA) to form an amic acid.
5. The amic acid is then thermally imidized to form a polyimide.
6. The polyimide is then cross-linked with heat and pressure to generate a thermoset network.

Examples of Thermosetting Polyimides Derived from Resveratrol

1. Resveratrol is isolated from plants by steam distillation or solvent extraction. In embodiments resveratrol is prepared via a biosynthetic route by conversion of sugars or lignocellulosic feedstocks with metabolically engineered organisms. In other embodiments resveratrol is prepared from renewable phenols as described in U.S. Pat. Nos. 9,187,591, 9,127,115, 9,051,414, 9,018, 314, 8,993,689, 8,993,688, 8,921,614. In other embodiments resveratrol is derived from petroleum sources.
2. Resveratrol is converted to a trisaniline by a variety of methods including, but not limited to a) Smiles rearrangement; b) conversion to a trisulfonate, trihalide, or triboronic ester, followed by transition metal catalyzed Buchwald Hartwig coupling with ammonia or primary amine precursors. In embodiments the reaction is carried out using Pd(dba)$_3$ as the catalyst and benzophenone imine as the amine precursor. In other embodiments resveratrol is hydrogenated with a heterogeneous or homogenous catalyst under a hydrogen atmosphere to generate dihydroresveratrol which is then converted to a saturated trisaniline as described above. In still other embodiments trans-resveratrol is isomerized to cis-resveratrol and then converted to a trisaniline.
3. Alternatively dihydroresveratrol is allowed to react with a halogenated nitroaromatic compound under basic conditions to generate a trinitro-compound. The trinitro-compound is then hydrogenated to a trisaniline.

4. A trisaniline is allowed to react with a tetracarboxylic dianhydride and a thermosetting endcap to generate an amic acid. In embodiments the tetracarboxylic dianhydride is 3,3',4,4'-benzophenonetetracarboxylic dianhydride (BTDA). In other embodiments the thermosetting endcap is 5-norbornene-2,3-dicarboxylic anhydride (nadic anhydride or NA). In embodiments the reaction stoichiometry is approximately 1:1:1 NA:BTDA:trisaniline.

6. The amic acid is then thermally imidized in air or nitrogen at moderate temperature~200-250° C. to generate a polyimide oligomer.

7. The polyimide oligomer is then further imidized and cross-linked with heat and pressure to generate a thermoset polyimide network. In embodiments, the cure reaction is conducted at temperatures from about 280-315 degrees C. In other embodiments the cure reaction is conducted under about 15-250 psi of pressure. In embodiments the cross-linked resin has a glass transition temperature greater than 320 degrees C. (as measured by Differential Scanning Calorimetry (DSC)). In embodiments the polyimide is combined with fibers including glass, carbon, and other fibers and cured as described above to form a composite material.

Preparation of trisanilines from resveratrol. Resveratrol can be converted to trisanilines via several routes. Three methods are depicted in FIG. 1 and examples 1-6. FIG. 1. Shows the synthesis of trisanilines from resveratrol.

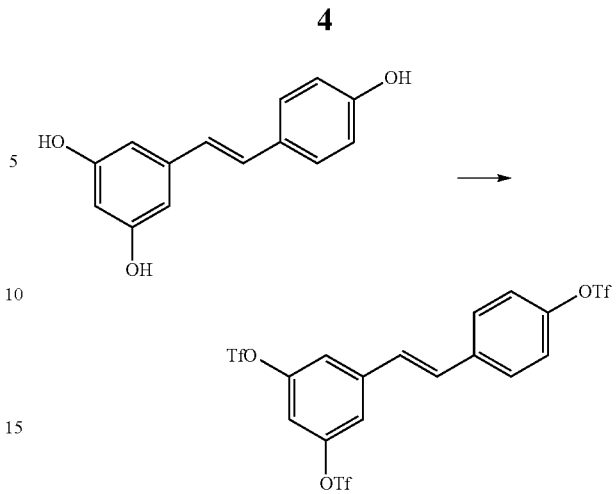

Example 1. Synthesis of resveratrol tristriflate: To a solution of 11.41 g resveratrol (50 mmol) and 21 mL pyridine (260 mmol, 5 eq) in 300 mL $CH_2Cl_2$ cooled to −30° C. was added 30 mL (178 mmol, 3.5 eq) triflic anhydride. The reaction was warmed and stirred overnight at ambient temperature. The reaction was then washed with water, 4 N HCl and 4 M NaOH, dried over $MgSO_4$ and concentrated to yield 29.24 g of a tan solid (94%). The material was recrystallized from 200 mL EtOH to afford 25.92 g of a yellow crystalline solid in 83% yield. Mp 98-99° C. $^1$H NMR ($CDCl_3$): 7.62 (d, 2H, J=8.9 Hz), 7.46 (d, 2H, J=7.3 Hz), 7.33 (d, 2H, J=8.9 Hz), 7.21-7.03 (m, 3H). $^{13}$C NMR ($CDCl_3$): 149.79, 149.54, 141.26, 135.97, 131.53, 128.67, 126.71, 121.95, 119.22 118.74 (q, J=321 Hz) 118.68 (q, J=321 Hz), 114.04. Calc for $C_{17}H_9F_9O_9S_3$: C, 32.70%; H, 1.28%; F, 27.24%; S, 15.40%. Found C, 32.81%; H, 1.28%; F, 27.24%; S, 15.30%.

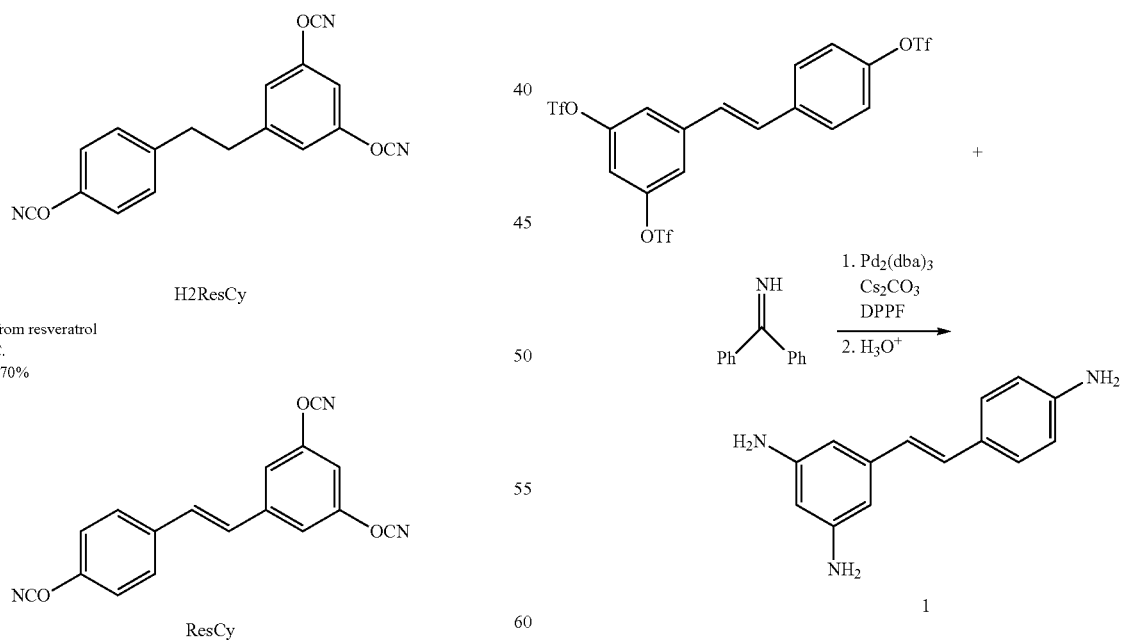

H2ResCy

Two steps from resveratrol
$T_g$ = 334° C.
Char yield: 70%

ResCy

One step from resveratrol
$T_g$ > 350° C.
Char yield: 74%
Extremely fire resistant
High water uptake, difficult to process Example 2. Synthesis of (E)-5-(4-aminostyryl)benzene-1,3-diamine (trisaminoresveratrol), compound 1: To a flame dried 3-neck round bottomed flask equipped with a reflux condenser under inert atmosphere, 0.95 g of tris(dibenzylidineacetone)dipalladium (1.0 mmol, 3.6 mol %), 45.56 g of cesium carbonate (143 mmol, 5 eq), and 1.90 g of 1,1'-bis (diphenylphosphino)ferrocene (3.4 mmol, 12 mol %) was added to 300 mL dry THF. Next, 28.56 g of benzophenone imine (142 mmol, 5 eq) and 17.90 g of resveratrol triflate (28.7 mmol) in dry THF were added via cannula and the reaction was heated to reflux for 72 hours. The reaction was then cooled to room temperature, filtered through celite, and concentrated under vacuum. The resulting residue was dissolved in 300 mL THF, followed by addition of 200 mL 4 N HCl. The reaction was then heated to reflux for 4 hours and allowed to cool to ambient temperature. The reaction was then washed with 300 mL $Et_2O$ and 300 mL $CH_2Cl_2$, and the aqueous phase was added to 250 mL of 4 N NaOH and ice, where an off-white (yellowish) solid precipitated out. The solids were filtered and dried to afford 8.24 g of an orange solid, which then underwent flash column silica gel chromatography (EtOAc followed by 2% MeOH/EtOAc) to afford 4.47 g (69% yield) of an off-white solid. Mp>170° C. (dec). $^1$H NMR (DMSO-$d_6$): 7.20 (d, 2H), 6.73 (d, 1H), 6.56 (d, 1H), 6.53 (d, 2H), 5.95 (s, 2H), 5.71 (s, 1H), 5.22 (s, 2H), 4.67 (s, 4H). $^{13}$C NMR (DMSO-$d_6$): 149.6, 148.8, 139.0, 127.7, 127.5, 125.6, 125.0, 114.4, 101.8, 99.9. GC/MS: 225 ($MI^+$).

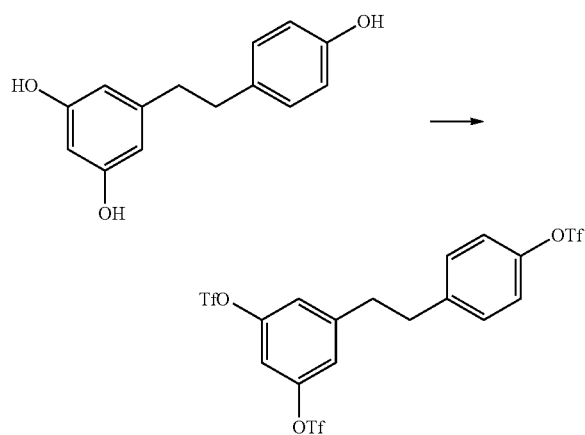

Example 3. Synthesis of dihydroresveratrol tristriflate: A solution of 10.55 grams dihydroresveratrol (46 mmoles) and 19 mL pyridine (235 mmoles, 5 eq) in 300 mL toluene was cooled to -30° C. while 27 mL triflic anhydride (160 mmoles, 3.5 eq) was added dropwise with mechanical stirring. The mixture was allowed to warm to room temperature and stirred overnight. The mixture was washed with 2×300 mL water and brine then dried ($MgSO_4$) and concentrated in vacuum to give 27.40 grams of an orange oil which crystallized on standing (95%). This was recrystallized from 25 mL toluene and 75 mL hexanes to give 20.82 grams of a tan solid (72%). Mp 38-39° C. $^1$H NMR ($CDCl_3$): 7.20 (s, 4H), 7.10 (s, 3H), 3.02 (m, 4H). Calc for $C_{17}H_{11}F_9O_9S_3$: C, 32.60%; H, 1.77%; F, 27.30%; S, 15.35%. Found: C, 32.71%; H, 1.61%; F, 27.15%; S, 15.12%.

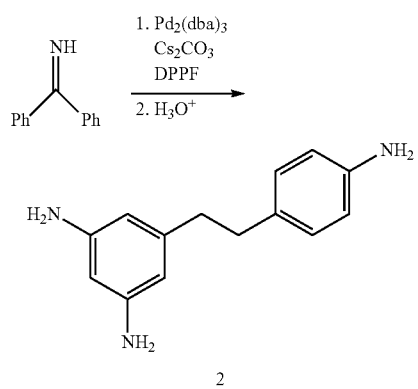

Example 4. Synthesis of 5-(4-aminostyryl)benzene-1,3-diamine (trisaminodihydroresveratrol), compound 2: To a flame dried 3-neck round bottomed flask equipped with a reflux condenser under inert atmosphere, 0.7 g of tris (dibenzylidine acetone)dipalladium (0.76 mmol, 3.6 mol %), 34.1 g cesium carbonate (105 mmol, 5 eq), and 1.39 g of 1,1'-bis(diphenylphosphino)ferrocene (2.5 mmol, 12 mol %) was added to 300 mL dry THF. Next, 21.1 g benzophenone imine (105 mmol, 12 mol %) and 13.11 g dihydroresveratrol tristriflate (20.9 mmol) in dry THF were added via cannula and the reaction was heated to reflux for 72 hours. The reaction was then cooled to room temperature, filtered through celite, and concentrated under vacuum. The resulting residue was dissolved in 250 mL THF, followed by addition of 150 mL 4N HCl. The reaction was then heated to reflux for 4 hours and allowed to cool to ambient temperature. The reaction was then washed with 250 mL $Et_2O$ and 250 mL $CH_2Cl_2$, and the aqueous phase was added to 200 mL of 4 N NaOH and ice. The reaction was then extracted twice with 150 mL portions of $CH_2Cl_2$. The organic phase was dried over magnesium sulfate and concentrated under vacuum resulting in 7.02 g of a brown solid. The solid then underwent flash silica gel column chromatography (EtOAc followed by 2% MeOH/EtOAc) to afford 2.57 g of an off-white solid in a 54% yield. Mp 135-140° C. This was recrystallized from 40 mL EtOAc to afford 1.93 g of a white solid in a 41% yield. Mp 140-143° C. $^1$H NMR (DMSO-$d_6$): 6.84 (d, 2H), 6.46 (d, 2H), 5.68 (d, 2H), 5.64 (t, 1H), 4.64 (s, 6H), 2.56 (m, 2H), 2.43 (m, 2H). $^{13}$C NMR (DMSO-d6): 149.34, 146.83, 143.20, 129.60, 128.97, 114.41, 103.89, 98.41, 38.81, 36.97. GC/MS: 227 ($MI^+$). Calc for $C_{14}H_{17}N_3$: C, 73.98%; H, 7.54%; N, 18.49%. Found C, 74.29%; H, 7.38%, N, 17.17%.

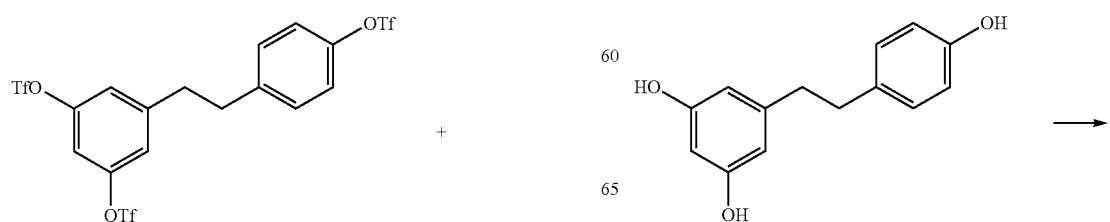

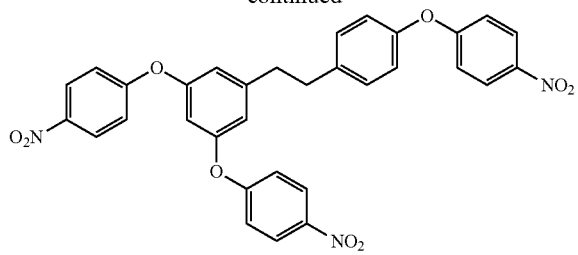

Example 5. Synthesis of 4,4'-((5-(4-(4-nitrophenoxy)phenethyl)-1,3-phenylene)bis(oxy))bis(nitrobenzene): A mixture of 2.5 grams dihydroveratrol (10.9 mmoles), 4.70 grams 4-fluoronitrobenzene (33.3 mmoles, 3 eq) and 5 grams $K_2CO_3$ (36 mmoles) in 30 mL NMP was heated to 150° C. and stirred overnight. The mixture was allowed to cool and poured into 300 mL ice water. The solids were filtered off and washed with water then dried to give 6.00 grams of a tan solid (100%). This was recrystallized from 125 mL toluene to give 4.88 grams of a tan solid (75%). mp 155-158° C. A second crop was isolated by adding 150 mL heptane to the mother liquor and cooling. This resulted in 0.62 grams of a tan solid (10%). mp 155-157° C. Total yield was 85%. $^1$H NMR ($CD_2Cl_2$): 8.23 (m, 6H), 7.21 (m, 2H), 7.04 (m, 8H), 6.75 (d, 3H), 3.01 (s, 4H). $^{13}$C NMR ($CD_2Cl_2$): 163.47, 162.56, 156.17, 152.96, 145.99, 143.08, 138.07, 130.37, 128.94, 128.14, 125.92, 120.54, 117.49, 117.23, 116.84, 110.23, 37.46, 36.57. Calc for $C_{32}H_{23}N_3O_9$: C, 64.75%; H, 3.91%; N, 7.08%; Found: C, 65.26/65.37%; H, 4.22/4.09%; N, 6.86/6.98%.

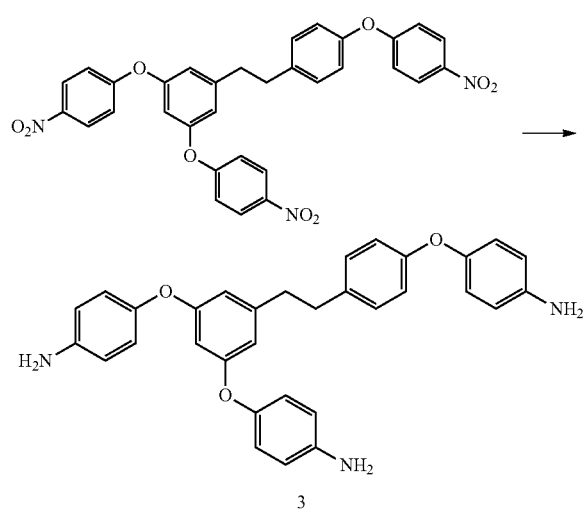

Example 6. Synthesis of 4,4'-((5-(4-(4-aminophenoxy)phenethyl)-1,3-phenylene)bis(oxy))bis(aniline), compound 3: To a Parr hydrogenation vessel was added 1.00 g (1.7 mmol) of 4,4'-((5-(4-(4-nitrophenoxy)phenethyl)-1,3-phenylene)bis(oxy))-bis(nitrobenzene) and 0.1 g 10% Pd/C in 100 mL of a 1:1 mixture of MeOH/Toluene. The reaction was hydrogenated at 50 psi. Theory was 1 psi drop, actual was 1.3 psi. The reaction was then filtered through celite and concentrated under vacuum to give 0.95 g of a dark brown, tacky, glassy solid. The solid was recrystallized from 30 mL of MeOH and 10 mL water to afford 0.70 g of a tan solid in an 82% yield. Mp 134-136° C. $^1$H NMR (DMSO-$d_6$): 7.06 (d, 2H), 6.64 ((m, 8H), 6.55 (m, 6H), 6.32 (d, 1H), 6.13 (t, 1H), 4.96 (d, 6H). $^{13}$C NMR ($CDCl_3$): 159.86, 156.93, 149.02, 148.35, 144.31, 142.68, 142.46, 135.17, 129.45, 121.06, 120.83, 117.27, 116.23, 116.20, 110.99, 104.44, 37.97, 36.66. Calc for $C_{32}H_{29}N_3O_3$: C, 76.32%; H, 5.80%; N, 8.34%. Found C: 76.34%; H, 5.89%; N, 8.25%.

Example 7. Amic Acid derived from (E)-5-(4-aminostyryl)benzene-1,3-diamine (trisaminoresveratrol): To an oven dried 3-neck round bottom flask equipped with a reflux condenser under inert atmosphere was added 3.29 g (10.2 mmol) benzophenone-3,3',4,4'-tetracarboxylic dianhydride (BTDA) and 1.68 g (10.2 mmol) cis-5-norbornene-endo-2,3-dicarboxylic anhydride (NA) in 50 mL dry MeOH. The reaction was refluxed for 2 hours and cooled ambient temperature. Next, 2.30 g (10.2 mmol) trisaminoresveratrol was added, and the reaction (turning orange) was stirred overnight at ambient temperature. 5-10 mL of THF was then added to dissolve solids on the side of the flask, and the reaction was stirred for 3-5 more hours. The solvents were then removed under reduced pressure, affording an orange solid in quantitative yield which was used as is, with the remainder being stored under $N_2$ and sequestered from light.

Example 8. Amic Acid derived from 5-(4-aminostyryl)benzene-1,3-diamine (trisaminodihydroresveratrol): To an oven dried 3-neck round bottom flask equipped with a reflux condenser under inert atmosphere was added 2.41 g (7.49 mmol) benzophenone-3,3',4,4'-tetracarboxylic dianhydride (BTDA) and 1.23 g (7.49 mmol) cis-5-norbornene-endo-2,3-dicarboxylic anhydride (NA) in 50 mL dry MeOH. The reaction was refluxed for 2 hours and cooled ambient temperature. Next, 1.70 g (10.2 mmol) dihydrotrisaminoresveratrol was added, and the reaction (turning yellow-orange) was stirred overnight at ambient temperature. 5-10 mL of THF was then added to dissolve solids on the side of the flask, and the reaction was stirred for 3-5 more hours. The solvents were then removed under reduced pressure, affording an orange solid in quantitative yield which was used as is, with the remainder being stored under $N_2$ and sequestered from light.

Example 9. The cis-isomer of compound 1 is prepared by UV irradiation of trans-resveratrol to generate cis-resveratrol. Reaction conditions similar to those described in example 2 then yield compound 4.

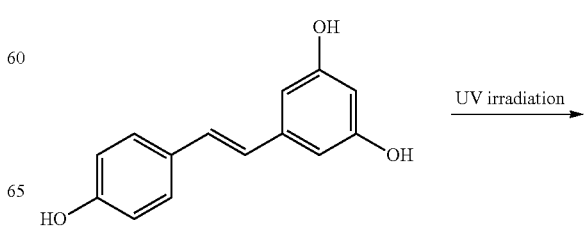

-continued

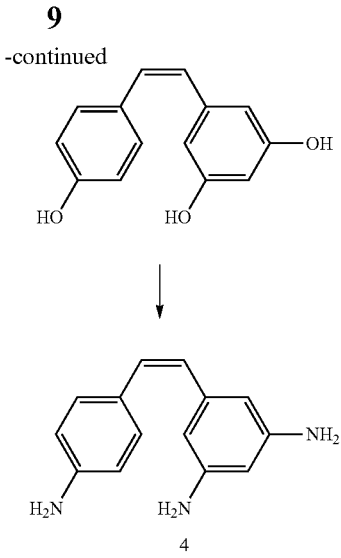

4

Figure 4:
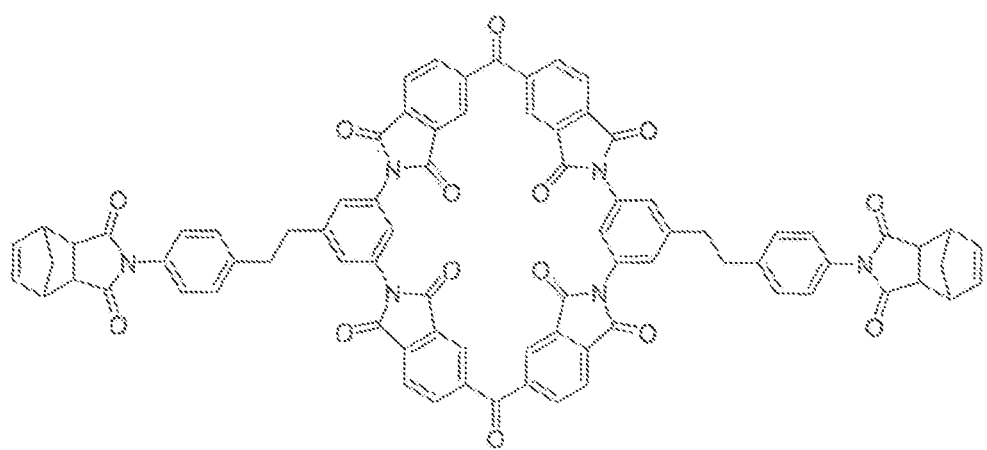
FIG. 4 is an idealized structure of a polyimide prepared from compound 2, BTDA (3,3',4,4'-benzophenone tetracarboxylic dianhydride), and nadic anhydride, according to embodiments of the invention.

Example 10. Polyimide oligomers are generated from the amic acids by thermal heating in the range of 200-230° C. for 2-3 h. An idealized example of a polyimide oligomer prepared from 2 is shown in FIG. 4.

Toxicity Testing. In vitro toxicity tests were conducted for compounds 1-3. Key results are listed in Table 1. Although 1 and 2 were shown to be mutagenic, they both have substantially reduced aquatic toxicity compared to MDA. Compound 3 was shown to be not mutagenic (Ames test) and had remarkably low aquatic toxicity.

TABLE 1

Toxicity Results for Trisanilines Derived from Resveratrol

| Aniline | Mutagenicity (Ames test) | Cytotoxicity | Aquatic Toxicity | LD50 |
|---|---|---|---|---|
| 1 | Mutagenic | >/=3.2 µg/mL | 1153 mg/L | 301 mg/kg |
| 2 | Mutagenic | >/=3.2 µg/mL | 52.7 mg/L | 820 mg/kg |
| 3 | Not mutagenic | None observed up to solubility limit (10 µg/mL) | >2000 mg/L | 568 mg/kg |
| MDA | Mutagenic | | 14.30 mg/L | 944 mg/kg |

Differential Scanning Calorimetry (DSC). DSC experiments were performed with a TA Instruments Q200 DSC. T-zero DSC pans were loaded with 10-20 mg of imide powder. The experiments were conducted under a nitrogen atmosphere. An initial ramp from ambient temperature up to 250° C. at 10° C./min was performed to eliminate any residual solvent or water and to allow the powder to flow and form good contact with the bottom of the pan. The samples were then equilibrated at 40° C. and ramped again at 10° C./min to 315° C. The material was then held isothermally for 2 h to promote cure, consistent with the typical cycle for PMR-15. Lastly, after equilibration at 40° C., a ramp to 400° C. at 10° C./min was utilized to measure the cured Tg.

Figure 2:
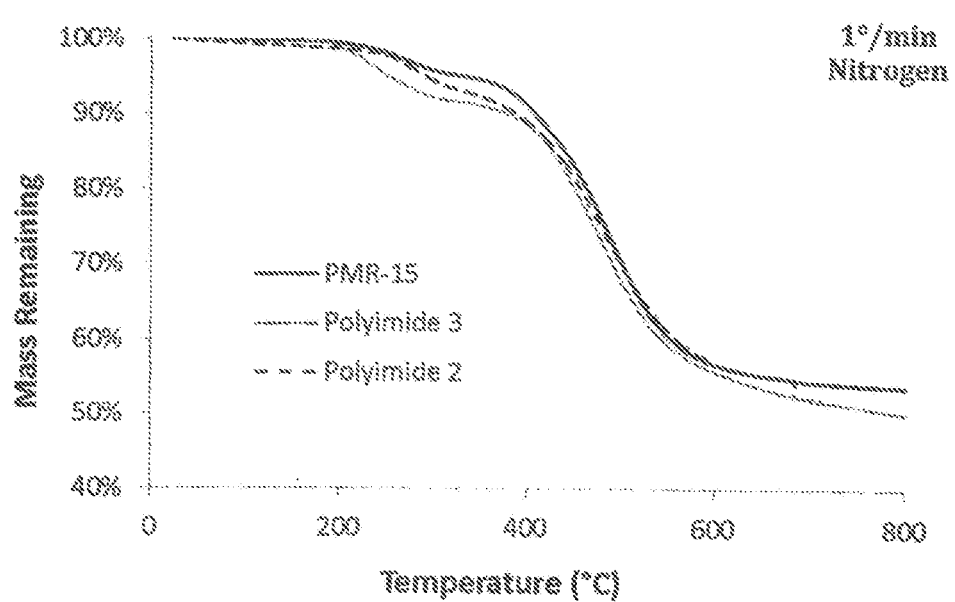
FIG. 2 is a graph showing the TGA data for PMR-15 and polyimides prepared from resveratrol trisanilines, according to embodiments of the invention.

Thermal Gravimetric Analysis (TGA). TGA experiments were performed using a TA Instruments Q5000 TGA under either air or nitrogen atmospheres. Temperature ramps were between 25° C. and 900° C. at a rate of 10° C./min. The temperatures at which 5 percent weight loss occurred (denoted $T_d$) were measured using the reduced mass obtained after curing was complete. TGA data for polyimide oligomers prepared from trisanilines 2 and 3 are shown in FIG. 2.

Figure 5:
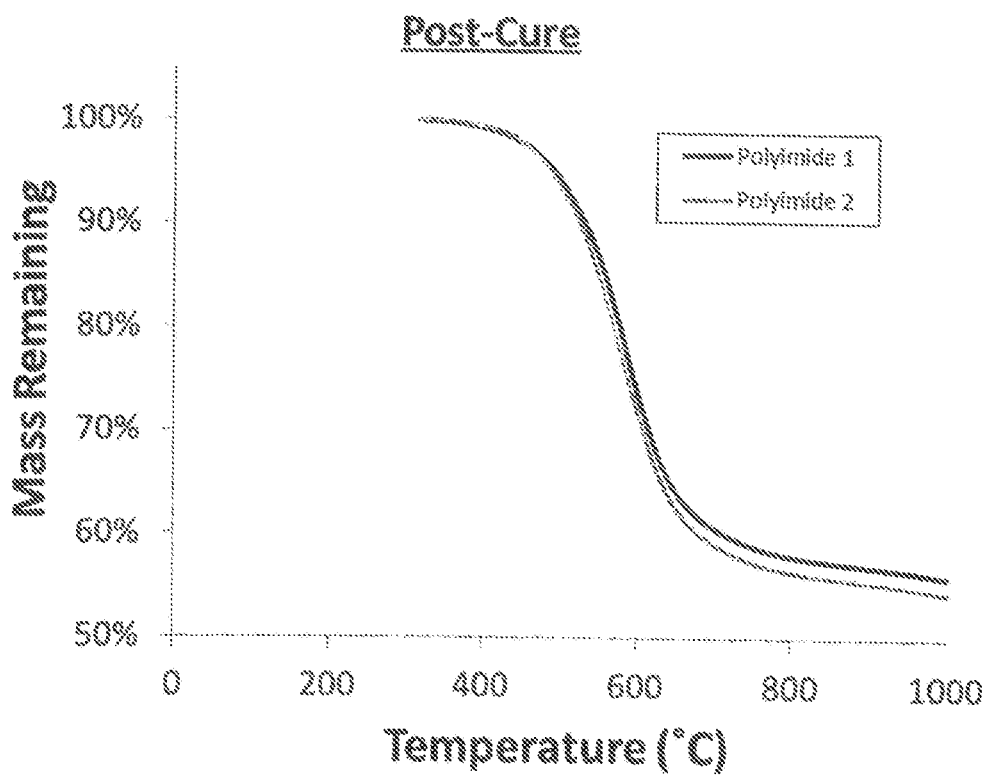
FIG. 5 is a graph showing the post-cure thermogravimetric analysis for polyimide 1 and 2, according to embodiments of the invention.
Figure 6:
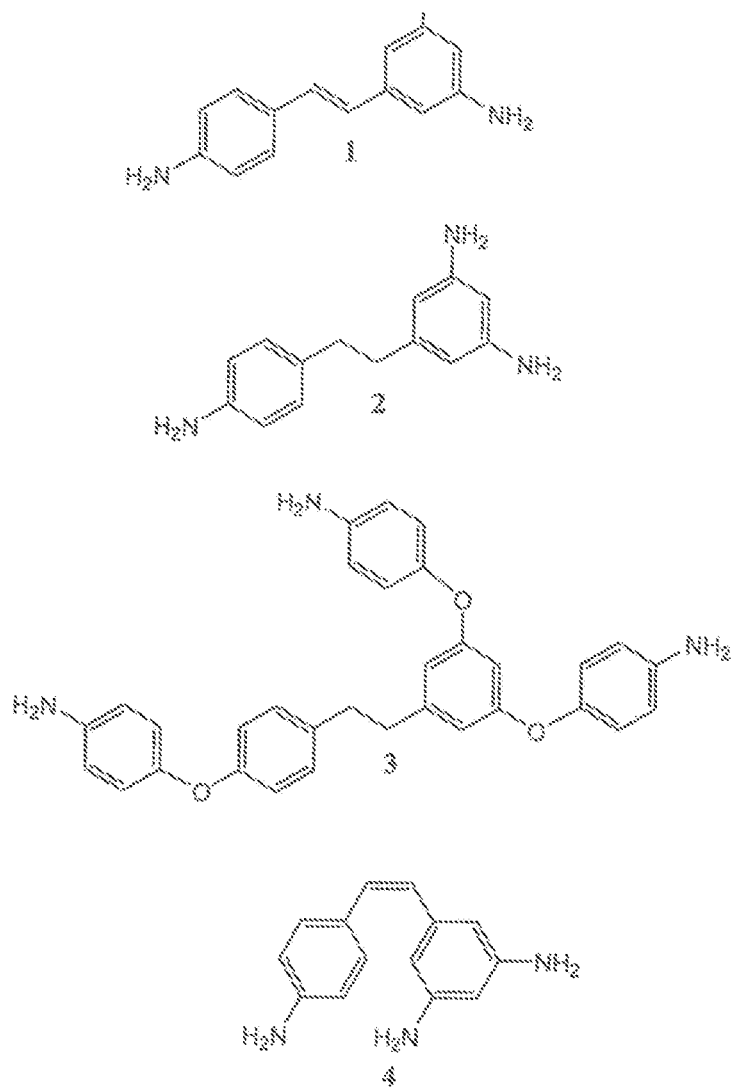
FIG. 6 is the trisanilines 1, 2, 3, and 4 from resveratrol, according to embodiments of the invention.

TGA data for cured polyimide thermosets prepared from trisanilines 1 and 2 are shown in FIG. 5.

Figure 3:
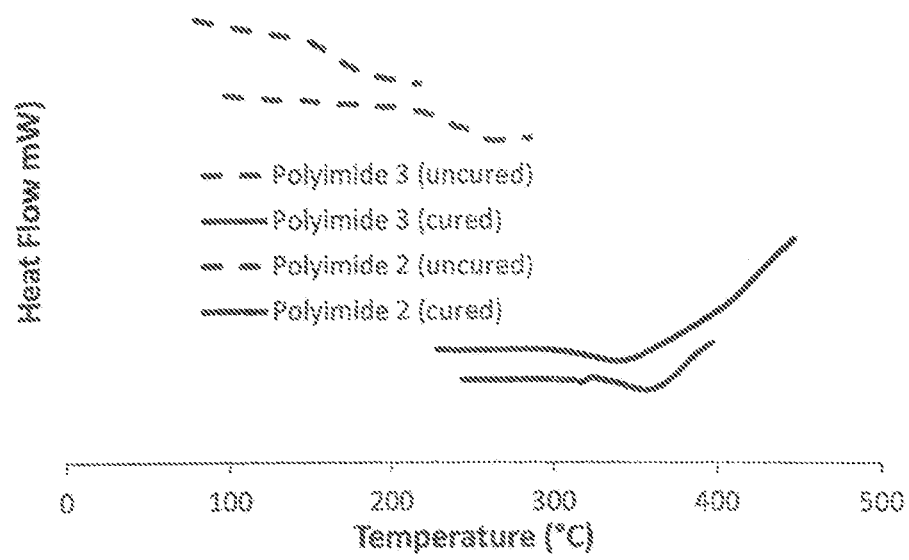
FIG. 3 is a graph showing the DSC data for trisanilines prepared from resveratrol, according to embodiments of the invention.

Amic acids prepared from anilines 1-3, BTDA, and NA in a ratio of approximately 1:1:1 were evaluated by DSC as described above. The data from these scans can be found in Table 2. FIG. 3 shows DSC data for cured polyimide thermosets derived from trisanilines 2 and 3. The decomposition temperature ($T_d$) defined as the temperature at which 5% mass loss is observed was measured by TGA and is included in Table 2.

TABLE 2

Glass transition temperatures and decomposition temperatures of polyimide thermosets prepared from 1-3

| Aniline | Pre-cure $T_g$(° C.) | Post-cure $T_g$ | $T_d$ (10° C./min, $N_2$) |
|---|---|---|---|
| 1 | >250 | 347 | 491 |
| 2 | 244 | 353 | 487 |
| 3 | 167 | 324 | 438 |

Embodiments of the invention includes methods for making thermosetting polyimides from resveratrol including, converting resveratrol to a trisaniline, reacting trisaniline with one or more dianhydrides and a thermosetting endcap to form an amic acid, thermally imidizing amic acid to form a polyimide oligomer, and cross-linking the polyimide oligomer with heat and pressure to generate a polyimide thermoset. Another aspect of the invention includes methods for making thermosetting polyimides from resveratrol including, reacting resveratrol with a halogenated nitroaromatic compound to form a trinitro-species, reducing trinitro-species to a trisaniline, reacting trisaniline with one or more dianhydrides and a thermosetting endcap to form an amic acid, thermally imidizing amic acid to form polyimide oligomers, and cross-linking polyimide oligomers with heat and pressure to generate polyimide thermosets. A method for making thermosetting polyimides from resveratrol including, converting resveratrol to a trisaniline, combining trisaniline with one or more polyanilines to obtain an aniline blend, reacting aniline blend with one or more dianhydrides and a thermosetting endcap to form an amic acid, thermally imidizing amic acid to form a polyimide oligomer, and cross-linking polyimide oligomer with heat and pressure to generate a polyimide thermoset.

In embodiments, the converting the resveratrol to a trisaniline is accomplished by the Smiles rearrangement or by conversion of the resveratrol to a trisulfonate, trihalide or triboronic ester followed by transition metal catalyzed Buchwald Hartwig coupling with ammonia or primary amine precursors. In other embodiments, the converting the resveratrol to a trisaniline is accomplished by utilizing Pd(dba)$_3$ as the catalyst, 1,1'-bis(diphenylphosphino)ferrocene as a ligand for Pd(dba)$_3$, and benzophenone imine as the amine precursor. In yet other embodiments, the converting the resveratrol to trisaniline is accomplished by hydrogenating the resveratrol with a heterogeneous catalyst under a hydrogen atmosphere to generate dihydroresveratrol and converting the dihydroresveratrol to a saturated trisaniline.

In embodiments, the dihydroresveratrol is allowed to react with a halogenated nitroaromatic compound under basic conditions to generate a trinitro-compound, where trinitro-compound is then hydrogenated to a trisaniline. In embodiments, the converting the resveratrol to a trisaniline is accomplished by isomerizing trans-resveratrol to cis-resveratrol with UV irradiation and converting the cis-resveratrol to a trisaniline. In embodiments, the dianhydride is a tetracarboxylic dianhydride. In embodiments, the tetracarboxylic dianhydride is 3,3',4,4'-benzophenonetetracarboxylic dianhydride (BTDA). In embodiments, the thermosetting encap is 5-norbornene-2,3-dicarboxylic anhydride.

In embodiments, the trisaniline is combined with the dianhydride and the thermosetting endcap with a reaction stoichiometry of about 1:1:1 of trisaniline:dianhydride:thermosetting endcap. In embodiments, the thermal imidizing of amic acid to form polyimide oligomers is conducted in air, nitrogen, or argon at temperatures of about 200° C. to about 250° C. In embodiments, the polyimide oligomers have number average molecular weights ranging from about 1300 to 4500 g/mol. In embodiments, the cross-linking of the polyimide oligomers is conducted at temperatures from about 280° C. to about 315° C. In embodiments, the polyimide thermosets are post-cured at temperatures ranging from about 315-350° C. In embodiments, the cross-linking is conducted at a pressure from about 15 psi to about 250 psi. In embodiments, the polyimide thermoset has a glass transition temperature greater than 320° C. as measured by Differential Scanning Calorimetry.

In embodiments, the thermosetting polyimides are combined with fibers including glass, quartz, carbon, and carbon nanotubes, and thermally cured to form a composite material. In embodiments, the converting the resveratrol to trisaniline includes a hydrogenation process. In other aspects of the invention, the thermosetting polyimides are processed by the methods herein. In yet other aspects of the inventions, the trisaniline has the structure of compound 1.

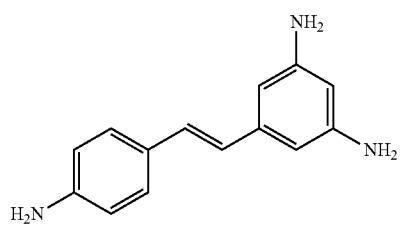

1

In other aspects of the invention, the trisaniline has the structure of compound 2.

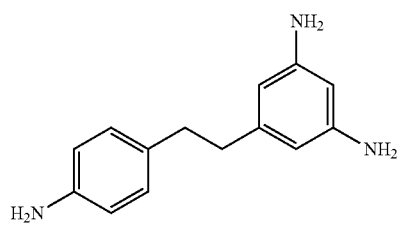

2

In other aspects of the invention, the trisaniline has the structure of compound 3.

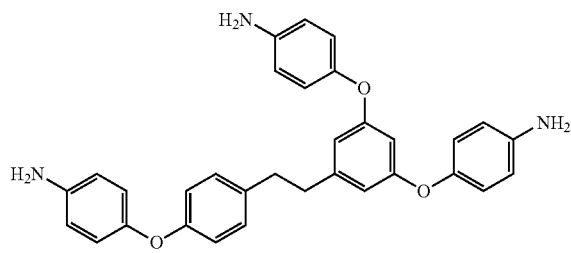 [SMILES: Nc1ccc(Oc2ccc(CCc3cc(Oc4ccc(N)cc4)cc(Oc4ccc(N)cc4)c3)cc2)cc1]

3

In other aspects of the invention, the trisaniline has the structure of compound 4.

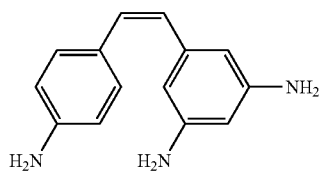

4

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:
1. A trisaniline having the formula:

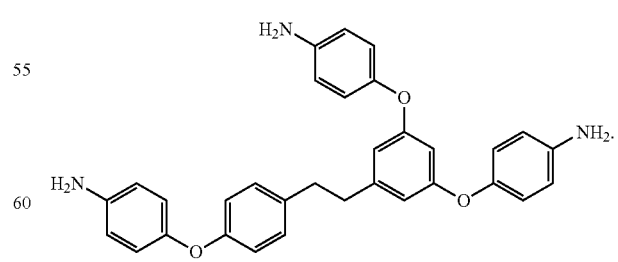

* * * * *